United States Patent [19]
LaFontaine et al.

[11] Patent Number: 6,092,526
[45] Date of Patent: Jul. 25, 2000

[54] PERCUTANEOUS CHAMBER-TO-ARTERY BYPASS

[75] Inventors: Daniel M. LaFontaine, Plymouth; Roger N. Hastings, Maple Grove; Thomas R. Hektner, Medina; Chad J. Kugler, Andover, all of Minn.

[73] Assignee: SCIMED Life Systems, Inc., Maple Grove, Minn.

[21] Appl. No.: 08/878,804

[22] Filed: Jun. 19, 1997

[51] Int. Cl.$^7$ .................................................... A61B 19/00
[52] U.S. Cl. .................. 128/898; 623/1; 623/11
[58] Field of Search ................. 623/2, 1, 11, 66; 128/898, 897; 604/7, 8, 9

[56] References Cited

U.S. PATENT DOCUMENTS

| | | | |
|---|---|---|---|
| Re. 35,352 | 10/1996 | Peters | 604/4 |
| Re. 35,459 | 2/1997 | Junkman | 604/164 |
| 3,667,069 | 6/1972 | Blackshear et al. | 3/1 |
| 4,016,884 | 4/1977 | Kwan-Gett | 128/348 |
| 4,165,747 | 8/1979 | Bermant | 128/334 |
| 4,173,981 | 11/1979 | Mortensen | 128/348 |
| 4,190,909 | 3/1980 | Ablaza | 3/1.4 |
| 4,230,096 | 10/1980 | Zeff et al. | 128/1 R |
| 4,546,499 | 10/1985 | Possis et al. | 623/1 |
| 4,562,597 | 1/1986 | Possis et al. | 623/1 |
| 4,566,453 | 1/1986 | Kumano et al. | 128/303.1 |
| 4,601,718 | 7/1986 | Possis et al. | 623/1 |
| 4,610,661 | 9/1986 | Possis et al. | 604/52 |
| 4,667,673 | 5/1987 | Li | 128/334 C |
| 4,690,684 | 9/1987 | McGreevy et al. | 623/12 |
| 4,710,192 | 12/1987 | Liotta et al. | 623/1 |
| 4,721,109 | 1/1988 | Healey | 128/334 R |

(List continued on next page.)

FOREIGN PATENT DOCUMENTS

| | | |
|---|---|---|
| 0 769 272 A1 | 4/1997 | European Pat. Off. . |
| WO 99/21490 | 5/1999 | European Pat. Off. . |
| WO 99/24102 | 5/1999 | European Pat. Off. . |
| 97-281410 | 7/1997 | Japan . |
| 308752 | 7/1971 | U.S.S.R. . |
| 388738 | 9/1971 | U.S.S.R. . |
| 891076 | 12/1981 | U.S.S.R. . |
| 1822750 A1 | 7/1982 | U.S.S.R. . |
| 1600708 | 12/1995 | U.S.S.R. . |
| WO 95/08364 | 3/1995 | WIPO . |
| WO 95/10218 | 4/1995 | WIPO . |
| WO 95/15192 | 6/1995 | WIPO . |
| WO 95/16476 | 6/1995 | WIPO . |
| WO 96/10375 | 4/1996 | WIPO . |
| WO 96/17644 | 6/1996 | WIPO . |
| WO 96/25886 | 8/1996 | WIPO . |
| WO 96/30072 | 10/1996 | WIPO . |
| WO 96/30073 | 10/1996 | WIPO . |
| WO 96/32882 | 10/1996 | WIPO . |

(List continued on next page.)

OTHER PUBLICATIONS

"The Possibility of Myocardial Revascularization by Creation of a Left Ventriculocronary Artery Fistula", Ian Munro and Peter Allen, Canada, pp. 25–32, Journal of Thoracic and Cardiovascular Surgery, vol. 58, No. 1, Jul. 1969.

"The Current Status of Lasers in the Treatment of Cardiovascular Disease" by Jeffrey M. Isner and Richard H. Clarke, *IEEE*, vol. QE–20, No. 12, Dec. 1984, pp. 1406–1420.

*Primary Examiner*—David H. Willse
*Assistant Examiner*—Dinh X. Nguyen
*Attorney, Agent, or Firm*—Westman, Champlin & Kelly, P.A.

[57] ABSTRACT

A vessel lies adjacent heart tissue, and a restriction in the vessel is bypassed. A chamber in the heart is accessed and a lumen is formed through the heart tissue which communicates with the vessel and a region distal to the restriction. Blood flows from the heart chamber into the vessel distal the restriction, thus bypassing the restriction.

3 Claims, 13 Drawing Sheets

U.S. PATENT DOCUMENTS

| | | | |
|---|---|---|---|
| 4,790,819 | 12/1988 | Li et al. | 604/59 |
| 4,803,984 | 2/1989 | Narayanan et al. | 128/334 R |
| 4,808,163 | 2/1989 | Laub | 604/105 |
| 4,819,640 | 4/1989 | Narayanan et al. | 128/334 R |
| 4,827,931 | 5/1989 | Longmore | 128/334 R |
| 4,907,591 | 3/1990 | Vasconcellos et al. | 606/154 |
| 4,911,164 | 3/1990 | Roth | 606/148 |
| 4,995,857 | 2/1991 | Arnold | 600/16 |
| 5,011,469 | 4/1991 | Buckberg et al. | 604/4 |
| 5,037,428 | 8/1991 | Picha et al. | 606/155 |
| 5,047,039 | 9/1991 | Avant et al. | 606/148 |
| 5,053,041 | 10/1991 | Ansari et al. | 606/148 |
| 5,053,043 | 10/1991 | Gottesman et al. | 606/148 |
| 5,061,245 | 10/1991 | Waldvogel | 604/170 |
| 5,067,958 | 11/1991 | Sandhaus | 606/142 |
| 5,080,663 | 1/1992 | Mills et al. | 606/144 |
| 5,080,664 | 1/1992 | Jain | 606/148 |
| 5,104,402 | 4/1992 | Melbin | 623/1 |
| 5,144,961 | 9/1992 | Chen et al. | 128/898 |
| 5,180,366 | 1/1993 | Woods | 604/96 |
| 5,222,962 | 6/1993 | Burkhart | 606/148 |
| 5,222,963 | 6/1993 | Brinkerhoff et al. | 606/153 |
| 5,222,971 | 6/1993 | Willard et al. | 606/158 |
| 5,234,445 | 8/1993 | Walker et al. | 606/148 |
| 5,254,113 | 10/1993 | Wilk | 606/8 |
| 5,256,141 | 10/1993 | Gencheff et al. | 604/53 |
| 5,281,236 | 1/1994 | Bagnato et al. | 606/139 |
| 5,282,810 | 2/1994 | Allen et al. | 606/150 |
| 5,287,861 | 2/1994 | Wilk | 128/898 |
| 5,308,320 | 5/1994 | Safar et al. | 604/4 |
| 5,314,436 | 5/1994 | Wilk | 606/153 |
| 5,314,472 | 5/1994 | Fontaine | 623/12 |
| 5,323,789 | 6/1994 | Berggren et al. | 128/898 |
| 5,330,486 | 7/1994 | Wilk | 606/139 |
| 5,370,683 | 12/1994 | Fontaine | 623/1 |
| 5,382,257 | 1/1995 | Lewis et al. | 606/148 |
| 5,383,854 | 1/1995 | Safar et al. | 604/98 |
| 5,383,928 | 1/1995 | Scott et al. | 623/1 |
| 5,397,345 | 3/1995 | Lazarus | 623/1 |
| 5,403,333 | 4/1995 | Kaster et al. | 606/151 |
| 5,409,019 | 4/1995 | Wilk | 128/898 |
| 5,423,744 | 6/1995 | Gencheff et al. | 604/53 |
| 5,425,705 | 6/1995 | Evard et al. | 604/28 |
| 5,425,739 | 6/1995 | Jessen | 606/155 |
| 5,429,144 | 7/1995 | Wilk | 128/898 |
| 5,433,700 | 7/1995 | Peters | 604/4 |
| 5,437,684 | 8/1995 | Calabrese et al. | 606/153 |
| 5,441,507 | 8/1995 | Wilk | 606/139 |
| 5,443,497 | 8/1995 | Venbrux | 623/1 |
| 5,447,512 | 9/1995 | Wilson et al. | 606/139 |
| 5,449,372 | 9/1995 | Schmaltz et al. | 606/198 |
| 5,452,733 | 9/1995 | Sterman et al. | 128/898 |
| 5,456,714 | 10/1995 | Owen | 623/1 |
| 5,472,404 | 12/1995 | Volgushev | 600/36 |
| 5,501,698 | 3/1996 | Roth et al. | 606/205 |
| 5,522,884 | 6/1996 | Wright | 623/2 |
| 5,527,319 | 6/1996 | Green et al. | 606/143 |
| 5,527,324 | 6/1996 | Krantz et al. | 606/155 |
| 5,527,337 | 6/1996 | Stack et al. | 606/198 |
| 5,536,251 | 7/1996 | Evard et al. | 604/93 |
| 5,540,677 | 7/1996 | Sinofsky | 606/8 |
| 5,540,701 | 7/1996 | Sharkey et al. | 606/153 |
| 5,545,171 | 8/1996 | Sharkey et al. | 606/148 |
| 5,554,162 | 9/1996 | DeLange | 606/153 |
| 5,556,414 | 9/1996 | Turi | 606/198 |
| 5,556,428 | 9/1996 | Shah | 623/13 |
| 5,562,728 | 10/1996 | Lazarus et al. | 623/1 |
| 5,569,272 | 10/1996 | Reed et al. | 606/151 |
| 5,569,274 | 10/1996 | Rapacki et al. | 606/158 |
| 5,571,090 | 11/1996 | Sherts | 606/144 |
| 5,571,215 | 11/1996 | Sterman et al. | 623/66 |
| 5,584,803 | 12/1996 | Stevens et al. | 604/4 |
| 5,588,949 | 12/1996 | Taylor et al. | 600/166 |
| 5,591,179 | 1/1997 | Edelstein | 606/144 |
| 5,591,212 | 1/1997 | Keimel | 607/5 |
| 5,593,424 | 1/1997 | Northrup, III | 606/232 |
| 5,601,576 | 2/1997 | Garrison | 606/148 |
| 5,601,581 | 2/1997 | Fogarty et al. | 606/159 |
| 5,609,598 | 3/1997 | Laufer et al. | 606/142 |
| 5,613,937 | 3/1997 | Garrison et al. | 600/201 |
| 5,618,270 | 4/1997 | Orejola | 604/164 |
| 5,643,292 | 7/1997 | Hart | 606/144 |
| 5,653,744 | 8/1997 | Khouri | 623/1 |
| 5,655,548 | 8/1997 | Nelson et al. | 128/898 |
| 5,662,124 | 9/1997 | Wilk | 128/898 |
| 5,662,711 | 9/1997 | Douglas | 623/12 |
| 5,676,670 | 10/1997 | Kim | 606/108 |
| 5,682,906 | 11/1997 | Sterrman et al. | 128/898 |
| 5,685,857 | 11/1997 | Negus et al. | 604/170 |
| 5,693,083 | 12/1997 | Baker et al. | 623/1 |
| 5,702,368 | 12/1997 | Stevens et al. | 604/171 |
| 5,702,412 | 12/1997 | Popov et al. | 606/159 |
| 5,715,832 | 2/1998 | Koblish et al. | 128/754 |
| 5,716,367 | 2/1998 | Koike et al. | 606/144 |
| 5,718,725 | 2/1998 | Sterman et al. | 623/2 |
| 5,722,426 | 3/1998 | Kolff | 128/898 |
| 5,725,537 | 3/1998 | Green et al. | 606/143 |
| 5,727,569 | 3/1998 | Benetti et al. | 128/898 |
| 5,728,151 | 3/1998 | Garrison et al. | 623/2 |
| 5,735,290 | 4/1998 | Sterman et al. | 128/898 |
| 5,738,649 | 4/1998 | Macoviak | 604/43 |
| 5,738,652 | 4/1998 | Boyd et al. | 604/96 |
| 5,749,892 | 5/1998 | Vierra et al. | 600/204 |
| 5,752,526 | 5/1998 | Cosgrove | 128/898 |
| 5,755,682 | 5/1998 | Knudson et al. | 604/8 |
| 5,755,687 | 5/1998 | Donlon | 604/53 |
| 5,755,778 | 5/1998 | Kleshinski | 623/1 |
| 5,758,663 | 6/1998 | Wilk et al. | 128/898 |
| 5,766,151 | 6/1998 | Valley et al. | 604/96 |
| 5,769,812 | 6/1998 | Stevens et al. | 604/4 |
| 5,788,979 | 8/1998 | Alt et al. | 424/426 |
| 5,792,094 | 8/1998 | Stevens et al. | 604/4 |
| 5,795,325 | 8/1998 | Valley et al. | 604/53 |
| 5,797,920 | 8/1998 | Kim | 606/108 |
| 5,797,933 | 8/1998 | Snow et al. | 606/151 |
| 5,799,661 | 9/1998 | Boyd et al. | 128/898 |
| 5,800,450 | 9/1998 | Lary et al. | 606/180 |
| 5,800,522 | 9/1998 | Campbell et al. | 623/1 |
| 5,836,311 | 11/1998 | Borst et al. | 128/897 |
| 5,849,036 | 12/1998 | Zarate | 623/1 |
| 5,855,210 | 1/1999 | Sterman et al. | 128/898 |
| 5,855,614 | 1/1999 | Stevens et al. | 623/11 |
| 5,906,607 | 5/1999 | Taylor et al. | 606/1 |
| 5,916,193 | 6/1999 | Stevens et al. | 604/53 |
| 5,921,979 | 7/1999 | Kovac et al. | 606/1 |
| 5,928,181 | 7/1999 | Coleman et al. | 604/8 |

FOREIGN PATENT DOCUMENTS

| | | |
|---|---|---|
| WO 97/12555 | 4/1997 | WIPO . |
| WO 97/13463 | 4/1997 | WIPO . |
| WO 97/13468 | 4/1997 | WIPO . |
| WO 97/13471 | 4/1997 | WIPO . |
| WO 97/26939 | 7/1997 | WIPO . |
| WO 97/37984 | 10/1997 | WIPO . |
| WO 97/40751 | 11/1997 | WIPO . |
| WO 98/06356 | 2/1998 | WIPO . |
| WO 98/07399 | 2/1998 | WIPO . |
| WO 98/10714 | 3/1998 | WIPO . |
| WO 98/15237 | 4/1998 | WIPO . |
| WO 98/16161 | 4/1998 | WIPO . |
| WO 98/16174 | 4/1998 | WIPO . |
| WO 98/17182 | 4/1998 | WIPO . |

| | | | | | | |
|---|---|---|---|---|---|---|
| WO 98/17187 | 4/1998 | WIPO . | | WO 98/57591 | 12/1998 | WIPO . |
| WO 98/19607 | 5/1998 | WIPO . | | WO 98/57592 | 12/1998 | WIPO . |
| WO 98/19634 | 5/1998 | WIPO . | | WO 99/04836 | 2/1999 | WIPO . |
| WO 98/19636 | 5/1998 | WIPO . | | WO 99/04845 | 2/1999 | WIPO . |
| WO 98/31302 | 7/1998 | WIPO . | | WO 99/35975 | 7/1999 | WIPO . |
| WO 98/32380 | 7/1998 | WIPO . | | WO 99/35977 | 7/1999 | WIPO . |
| WO 98/35626 | 8/1998 | WIPO . | | WO 99/35978 | 7/1999 | WIPO . |
| WO 98/37814 | 9/1998 | WIPO . | | WO 99/35979 | 7/1999 | WIPO . |
| WO 98/51223 | 11/1998 | WIPO . | | WO 99/35980 | 7/1999 | WIPO . |
| WO 98/52474 | 11/1998 | WIPO . | | WO 99/36000 | 7/1999 | WIPO . |
| WO 98/52475 | 11/1998 | WIPO . | | WO 99/36001 | 7/1999 | WIPO . |
| WO 98/57590 | 12/1998 | WIPO . | | | | |

PERCUTANEOUS CHAMBER-TO-ARTERY BYPASS

INCORPORATION BY REFERENCE

The following U.S. patent applications are hereby fully incorporated:

U.S. patent application Ser. No. 08/878,933, entitled PERCUTANEOUS ARTERY TO ARTERY BYPASS USING HEART TISSUE AS A PORTION OF A BYPASS CONDUIT, filed on even date herewith and assigned to the same assignee as the present application, still pending;

U.S. patent application Ser. No. 09/088,496, entitled PERCUTANEOUS CORONARY ARTERY BYPASS THROUGH A VENOUS VESSEL, filed on even date herewith and assigned to the same assignee as the present application, still pending;

U.S. patent application Ser. No. 08/813,038, entitled SYSTEM AND METHOD FOR PERCUTANEOUS CORONARY ARTERY BYPASS, filed on Mar. 6, 1997 and assigned to the same assignee as the present application, still pending;

U.S. patent application Ser. No. 08/813,040, entitled PERCUTANEOUS BYPASS WITH BRANCHING VESSEL, filed on Mar. 6, 1997 and assigned to the same assignee as the present application, still pending; and U.S. patent application Ser. No. 08/812,879, entitled PERCUTANEOUS BYPASS BY TUNNELING THROUGH VESSEL WALL, filed on Mar. 6, 1997 and assigned to the same assignee as the present application, still pending.

BACKGROUND OF THE INVENTION

The present invention generally deals with vascular bypass methods. More specifically, the present invention deals with systems for performing percutaneous coronary artery bypass procedures.

Coronary arteries can become partially restricted (stenotic) or completely clogged (occluded) with plaque, thrombus, or the like. This reduces the efficiency of the heart, and can ultimately lead to a heart attack. Thus, a number of different systems and methods have been developed for treating stenotic or occluded coronary arteries.

Two methods which have been developed to treat occlusions and stenosis include balloon angioplasty and pharmacological treatment. However, where the occlusion is quite hard, it can be quite difficult, if not impossible, to cross the occlusion with an angioplasty device. In addition, some coronary stenosis are too diffuse to treat effectively with balloon angioplasty. Unfortunately, such occlusions are not readily susceptible to dissolution with chemicals either. In the past, patients with these types of occlusions have been candidates for open heart surgery to bypass the restrictions.

However, open heart surgery includes a myriad of disadvantages. Open heart surgery typically includes a great deal of postoperative pain. The pain is normally encountered because conventional open heart surgery requires that the sternum be cracked open, which is quite painful. Also, open heart surgery typically involves bypassing the occluded vessel, which, in turn, involves harvesting a vein from another part of the body for use as the bypass graft. One common source for the bypass graft is the saphenous vein which is removed from the leg. Harvesting the saphenous vein requires the surgeon to cut and peel the skin back from an area of the leg which is approximately 18 inches long and which extends upward to the groin area. This can be very traumatic and painful. Also, the internal mammary artery (IMA) has also been used as a vein graft in performing a bypass. However, the IMA is typically best suited for use as a left anterior descending (LAD) vein graft and is commonly saved for that purpose. Further, open heart surgery requires quite a lengthy recovery period which involves an increased hospital stay, and, consequently, greater expense.

Other than the pain and more lengthy hospital stay, open heart surgery involves other disadvantages as well. For example, during open heart surgery, it is common to cool the heart to a point where it stops. The blood from the remainder of the vasculature is then pumped through a pulmonary and cardiac bypass system. Any time the heart is stopped, there is a danger of encountering difficulty in restarting the heart (which is typically accomplished by warming the heart and massaging it). Further, even if the heart is restarted, it sometimes does not return to a correct rhythm. Also, open heart surgery can require the use of a device known as a left ventricular assist device (LVAD) to supplementarily pump blood to relieve the burden on the heart. This allows the heart to heal.

A significant reason that the heart is typically stopped during open heart surgery is that, if it were not stopped, the surgeon would be working in a dynamic environment. In such an environment, the target vessels and tissue to be treated are moving. Further, a system must be employed in such an environment to stop bleeding. Clinical studies indicate that, when blood flow is stopped using clamping devices and blood flow is diverted to a cardiac bypass system, a statistically significant instance of neurological problems caused by blood clotting results. The use of mechanical clamps to stop blood flow, and the use of a mechanical bypass system, results in an approximate six percent instance of neurological problems, such as stroke, memory failure, etc.

Given the difficulties of the techniques discussed above, another approach has been developed which does not require stoppage of the heart or an open chest during execution. This approach is to perform a bypass using a minimally invasive technique by entering the upper chest cavity, through a hole between ribs under visual observation. Such a technique is often referred to as minimally invasive direct coronary artery bypass (MIDCAB) (where the heart is not stopped) or heart port (where the heart is stopped). Such a system which is used to perform a bypass is disclosed in the Sterman et al. U.S. Pat. No. 5,452,733.

SUMMARY OF THE INVENTION

A vessel lies adjacent heart tissue, and a restriction in the vessel is bypassed. A chamber in the heart is accessed and a lumen is formed through the heart tissue which communicates with the vessel and a region distal to the restriction. Blood flows from the heart chamber into the vessel distal of the restriction, thus bypassing the restriction.

BRIEF DESCRIPTION OF THE DRAWINGS

FIGS. 5A–5J illustrate a partially sectioned view of the heart of FIG. 1 and other steps of preferred embodiments in accordance with the present invention.

DETAILED DESCRIPTION OF THE PREFERRED EMBODIMENTS

Figure 1:
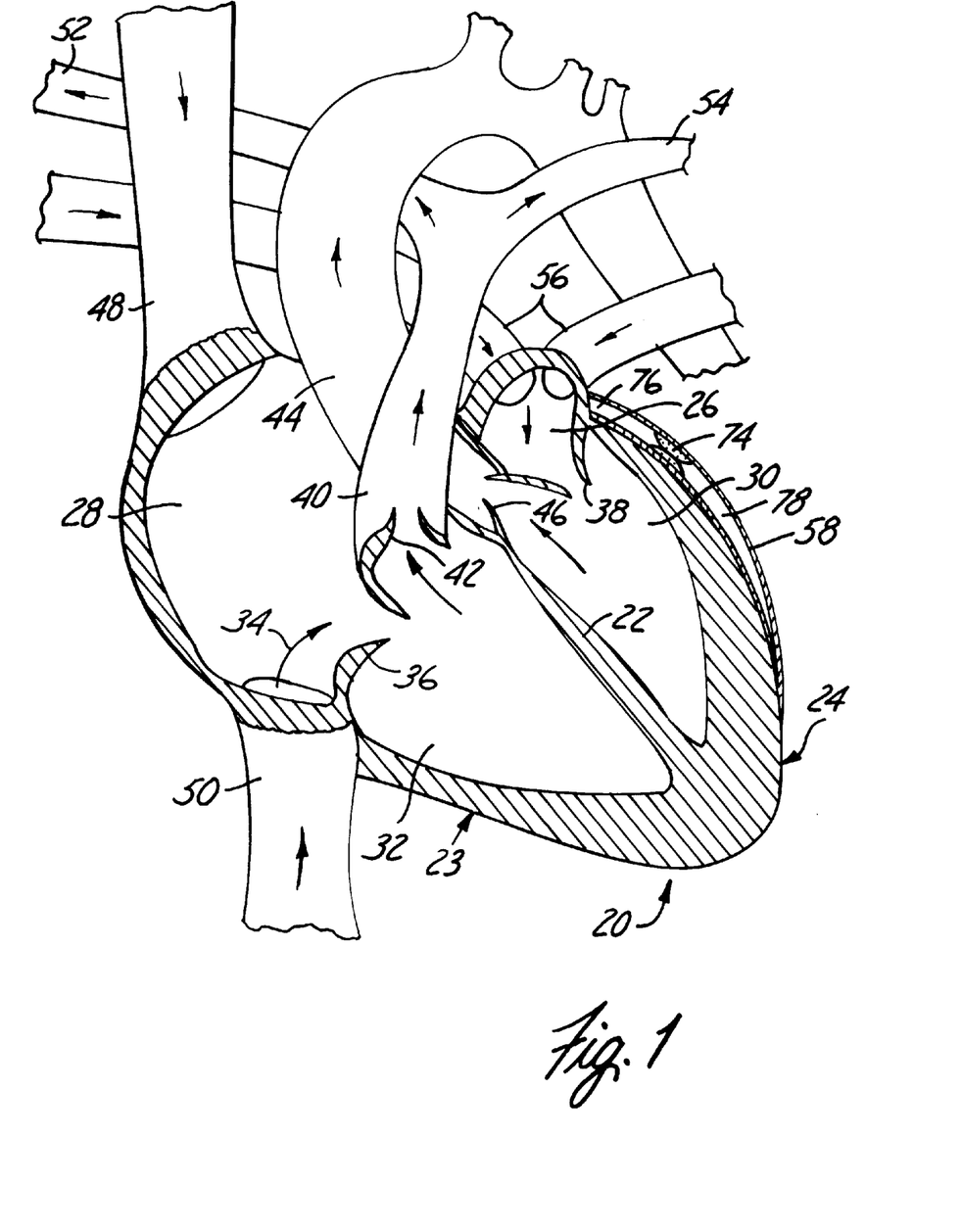
FIG. 1 illustrates a partial sectional view of a human heart and its associated proximate vascular system with a coronary artery having a restriction.

FIG. 1 illustrates a partially sectioned view of a human heart 20, and its associated vasculature. The heart 20 is subdivided by muscular septum 22 into two lateral halves, which are named respectively right 23 and left 24. A transverse constriction subdivides each half of the heart into two cavities, or chambers. The upper chambers consist of the left and right atria 26, 28 which collect blood. The lower chambers consist of the left and right ventricles 30, 32 which pump blood. The arrows 34 indicate the direction of blood flow through the heart. The right atrium 28 communicates with the right ventricle 32 by the tricuspid valve 36. The left atrium 26 communicates with the left ventricle 30 by the mitral valve. The right ventricle 32 empties into the pulmonary artery 40 by way of the pulmonary valve 42. The left ventricle 30 empties into the aorta 44 by way of the aortic valve 46.

The circulation of the heart 20 consists of two components. First is the functional circulation of the heart 20, i.e., the blood flow through the heart 20 from which blood is pumped to the lungs and the body in general. Second is the coronary circulation, i.e., the actual blood supply to the structures and muscles of the heart 20 itself.

The functional circulation of the heart 20 pumps blood to the body in general, i.e., the systematic circulation, and to the lungs for oxygenation, i.e., the pulmonic and pulmonary circulation. The left side of the heart 24 supplies the systemic circulation. The right side 23 of the heart supplies the lungs with blood for oxygenation. Deoxygenated blood from the systematic circulation is returned to the heart 20 and is supplied to the right atrium 28 by the superior and inferior venae cavae 48, 50. The heart 20 pumps the deoxygenated blood into the lungs for oxygenation by way of the main pulmonary artery 40. The main pulmonary artery 40 separates into the right and left pulmonary arteries, 52, 54 which circulates to the right and left lungs, respectively. Oxygenated blood returns to the heart 20 at the left atrium 26 via four pulmonary veins 56 (of which two are shown). The blood then flows to the left ventricle 30 where it is pumped into the aorta 44, which supplies the body with oxygenated blood.

The functional circulation, however, does not supply blood to the heart muscle or structures. Therefore, functional circulation does not supply oxygen or nutrients to the heart 20 itself. The actual blood supply to the heart structure, i.e., the oxygen and nutrient supply, is provided by the coronary circulation of the heart, consisting of coronary arteries, indicated generally at 58, and cardiac veins. Coronary artery 58 can have a restriction 74. The coronary artery 58 includes a proximal arterial bed 76 between the aorta 44 and the restriction 74. Also, the coronary artery 58 includes a distal arterial bed 78 downstream from the restriction 74.

Figure 2:
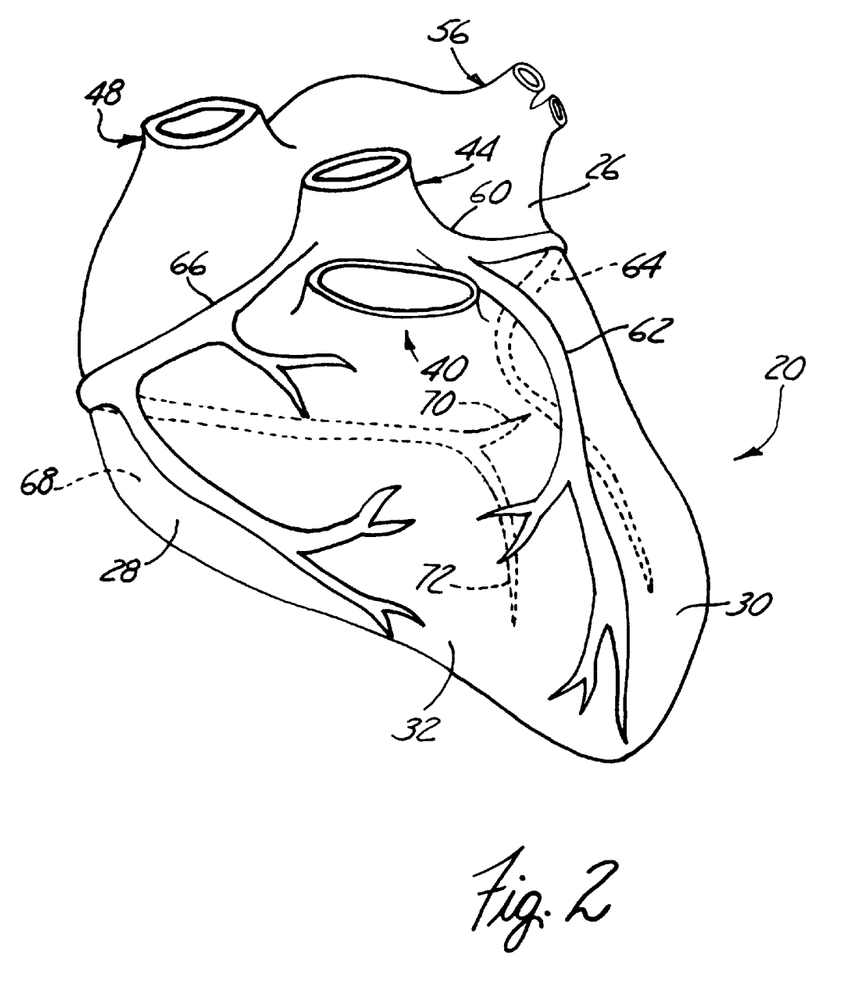
FIG. 2 illustrates a view of the heart of FIG. 1 with the major coronary arteries indicated thereon.

FIG. 2 shows the main coronary arteries of the heart 20. There are two main coronary arteries arising from the base of the aorta 44 and running along the heart 20 itself. The left main coronary artery 60 bifurcates into a left anterior descending branch 62 and the left circumflex branch 64. The left coronary artery 60 supplies the left atrium 26, gives branches to both ventricles 30, 32, and numerous small branches to the pulmonary artery 40. The right main coronary artery 66 runs along the posterior surface 68 of the heart 20 where it divides into a transverse branch 70 and a descending branch 72. The right coronary artery 66 supplies blood to the posterior aspect of the left ventricle 30. Both coronary arteries include a plurality of marginal branches, indicated only generally in the Figure. Coronary artery 58 is a generalized view of the arteries shown in FIG. 2, inasmuch as a restriction can occur in any coronary artery.

Figure 3:
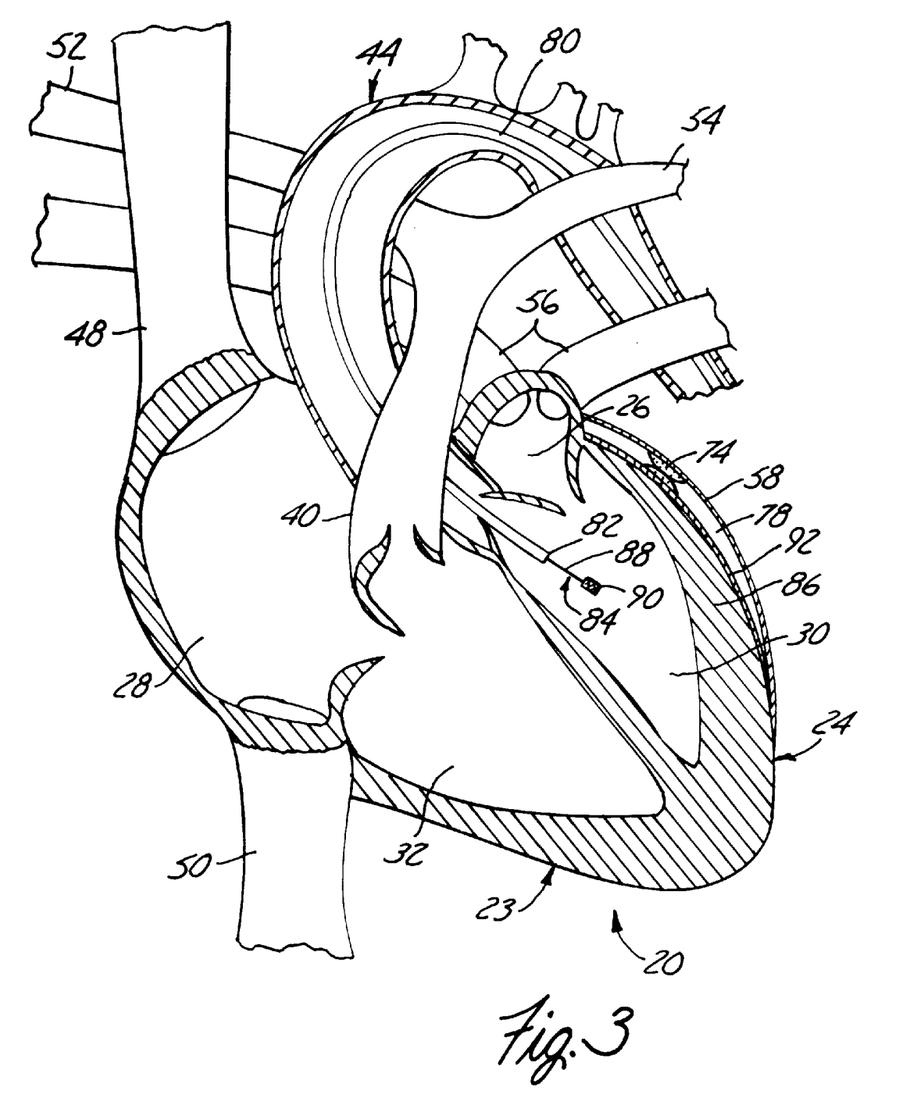
FIG. 3 illustrates a boring device accessing a chamber of the heart of FIG. 1.

FIG. 3 illustrates a first step utilized in accordance with the present invention to bypass restriction 74 in artery 58. A standard guide catheter 80 is advanced through aorta 44 in a known manner. Guide catheter 80 is positioned such that its distal end 82 is located within a chamber proximate the artery 58. In the preferred embodiment shown in the Figure, the distal end 82 of guide catheter 80 is positioned in the left ventricle 30. Cutting or debulking device 84 is then advanced through guide catheter 80, out through distal end 82 of guide catheter 80 to a region opposite the heart tissue 86 from the distal arterial bed 78 of the coronary artery 58. Cutting device 84, in the preferred embodiment, includes a catheter portion 88 and a boring or cutting member 90. Boring or cutting member 90 can take any number of suitable forms, such as a rotatable member or blade which can be used in piercing and boring through tissue. It should be noted that cutting device 84 can be any suitable mechanical cutting device, or any suitable sort of energy device, such as a radio frequency (RF) ablation wire, or a laser, or other device. A combination of devices could also be used. For example, an RF ablation wire can be used to form a small lumen suitable to accommodate a guidewire. A rotary device can then be used to widen out the lumen to its desired final size. In any case, the cutting device 84 is used to fashion a lumen through the heart tissue 86 and the vessel wall 92 of the coronary artery 58 so that the left ventricle 30 communicates with the distal arterial bed 78.

Alternatively, cutting device 84 can be used to form the lumen through heart tissue 86 starting from coronary artery 58. In that instance, cutting device 84 is used to cross restriction 74 and is then manipulated to cut through vessel wall 92 and heart tissue 86 so that the ventricle communicates with distal arterial bed 78.

Figure 4:
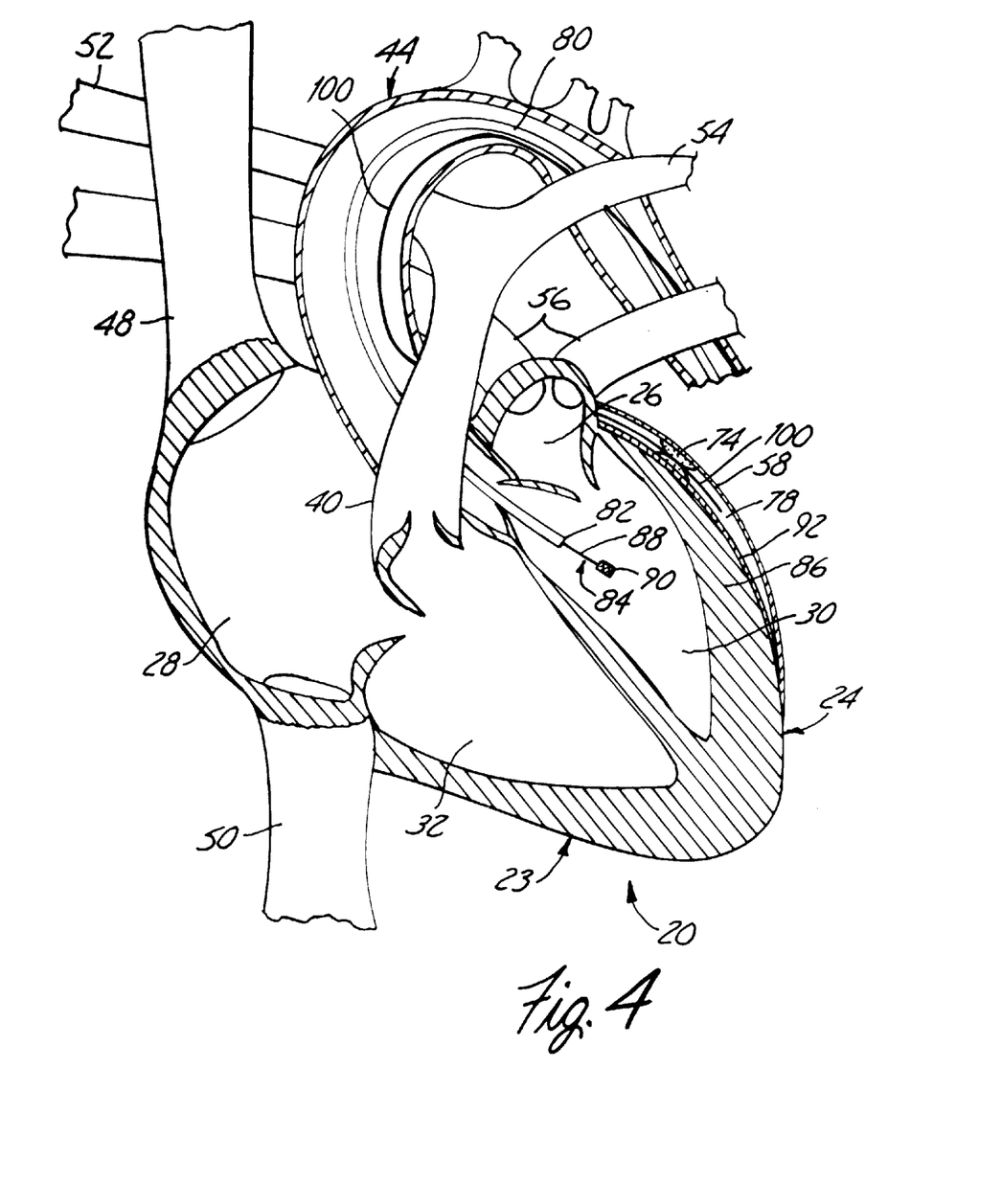
FIGS. 4–5J illustrate a partially sectioned view of the heart of FIG. 1 and other steps of preferred embodiments in accordance with the present invention.

In another embodiment, as illustrated in FIG. 4, restriction 74 is crossed with a conductive wire or fiber 100. Either the conductive wire or fiber residing in distal arterial bed 78, or cutting device 84, are provided with a transmitter, and the other (either the wire or fiber 100 which has been used to cross restriction 74, or cutting device 84) is provided with a receiver or sensor. In one preferred embodiment, the transmitter includes an array of active transmitters comprising one of ultrasound transmitters, radiofrequency transmitters, a plurality of point light sources, or a single intense point light source, or an electromagnetic transmitter (such as where current is actively applied to a coil to induce a magnetic field thereabout). The receiver, or sensor, is a suitable device which is compatible with the transmitter so that it can receive or sense the signals provided by the transmitter.

For instance, where the transmitter includes an inductive magnetic coil, the receiver includes a magnetic sensor array to receive the signals induced in the coil. When the transmitter includes an ultrasound transmitter, the receiver includes an ultrasound imager so that the relative positioning of the receiver device in the transmitter can be determined. When the transmitter includes a single point light source, or an array of point light sources, the receiver or sensor includes a photodiode array or an imaging fiber optic bundle which can detect the light emitted by the light sources. In addition, when the transmitter includes an RF transmitter, the receiver includes a directional antenna. In any of the above cases, or similar cases, the relative position between the transmitter and receiver can be determined so that the cutting member 90 of cutting device 84 can be properly located relative to the heart tissue 86 such that the cutting member 90 enters the coronary artery 58 in the distal arterial bed 78.

Figure 5:
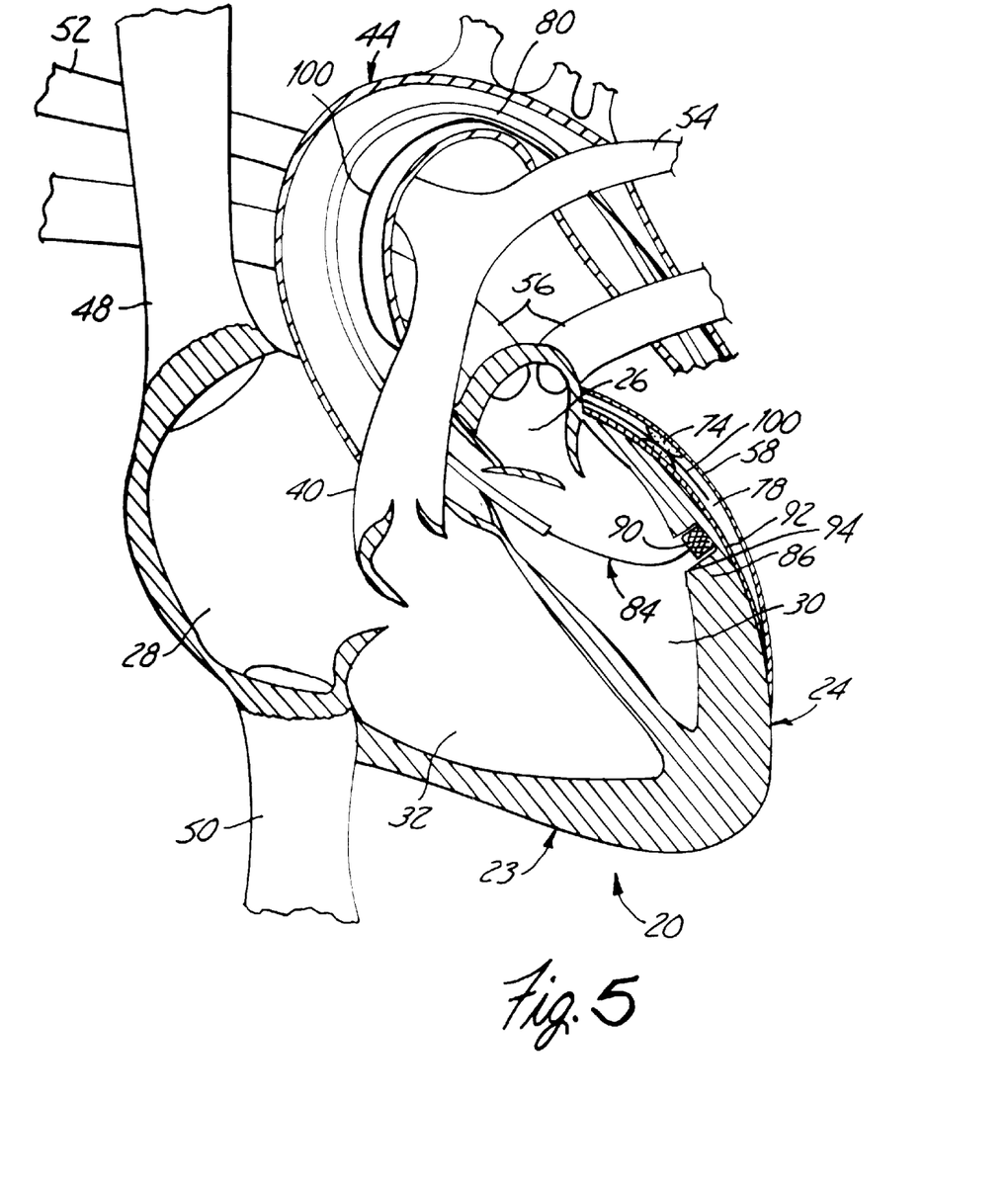

FIG. 5 illustrates the use of cutting device 84 to fashion a lumen 94 through heart tissue 86 and vessel wall 92 into the distal arterial bed 78. In a preferred embodiment, aspiration is provided during the cutting operation to remove severed tissue pieces. Such aspiration is preferably accompanied by saline infusate to flush the area around cutting member 90. Aspiration can be provided using any suitable known technique, such as an aspiration catheter.

Cutting device 84 can be guided through the heart tissue 86 and vessel wall 92 in any number of suitable ways from the left ventricle 30 to the distal arterial bed 78. For instance, the cutting member 90 of cutting device 84 is preferably formed of radiopaque material or has radiopaque markings thereon. Therefore, when restriction 74 is not a total occlusion, contrast fluid is injected through the coronary artery 58 to locate restriction 74. The relative position of the restriction 74 and cutting device 84 is then observed.

In another embodiment, radiopaque markers are placed in the distal arterial bed 78. Bi-plane fluoroscopy is then used to perform three dimensional visualization of the markers in the coronary artery 58 and on cutting member 90 to bring them toward one another.

Figure 5A:
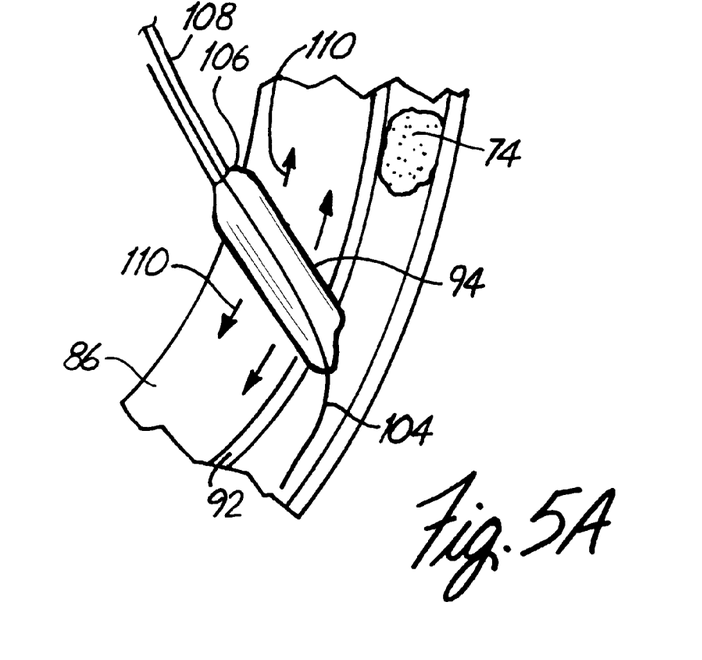

FIG. 5A illustrates another system for forming lumen 94 through heart tissue 86 in accordance with another aspect of the present invention. In the embodiment shown in FIG. 5A, a relatively small diameter device, such as an RF ablation wire, is used to first form a small lumen through heart tissue 86 and vessel wall 92. Then, guidewire 104 is passed through the small lumen and through vessel wall 92 into the portion of the vessel distal of the restriction. An inflatable balloon 106, preferably supported by a balloon catheter 108, is then advanced along guidewire 104 into the narrow lumen in heart tissue 86 and vessel wall 92. During insertion, balloon 106 is preferably in a deflated position. Once in place in the narrow lumen, balloon 106 is inflated thereby exerting axial force in the direction generally indicated by arrows 110 on the heart tissue and vessel wall 92. This operates to widen out the lumen to a desired size.

Figure 5B:
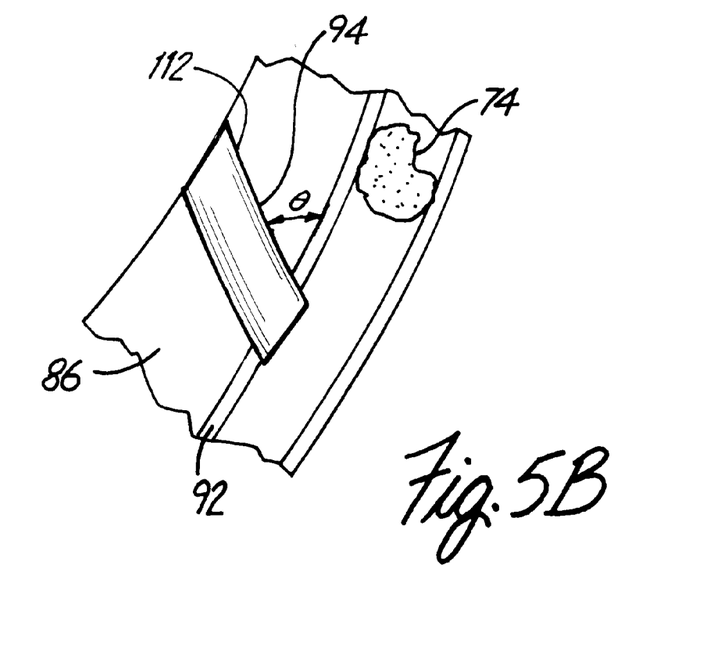

FIG. 5B illustrates yet another step in forming lumen 94 in accordance with another aspect of the present invention. After a suitable lumen is formed in heart tissue 86 and vessel wall 92 (either narrow, or a wider lumen), a stent 112 is delivered to the lumen and deployed (or expanded) to hold the lumen open to a desired dimension. Preferably lumen 94 is disposed at an angle θ of approximately 45° relative to vessel wall 92. This increases the chance of long term patency.

Figure 5C:
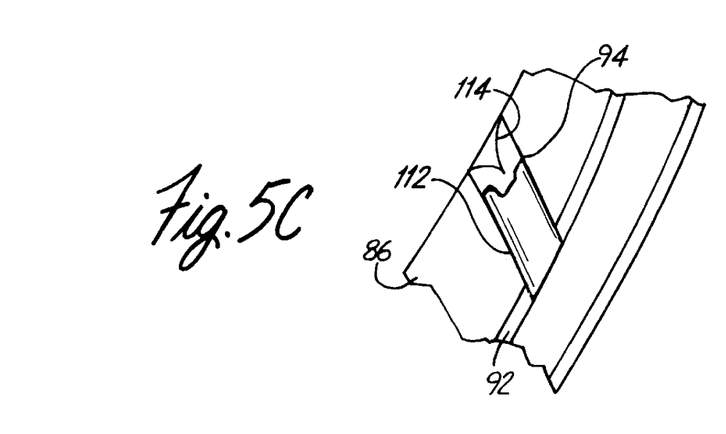

In yet another preferred embodiment, as shown in FIG. 5C, stent 112 also includes one-way valve 114. One-way valve 114 (or check valve 114) enables flow from the heart chamber to the restricted vessel during systole, but prevents back-flow into the chamber from the vessel during diastole. In the preferred embodiment, valve 114 is premounted on stent 112, prior to deployment. Then, the stent 112 and valve 114 assembly is delivered to the lumen 94 via a balloon delivery system which is introduced into the heart chamber. The delivery system is guided to the target and introduced into lumen 94 where the balloon in the stent delivery system is inflated to deploy stent 112.

Figure 5D:
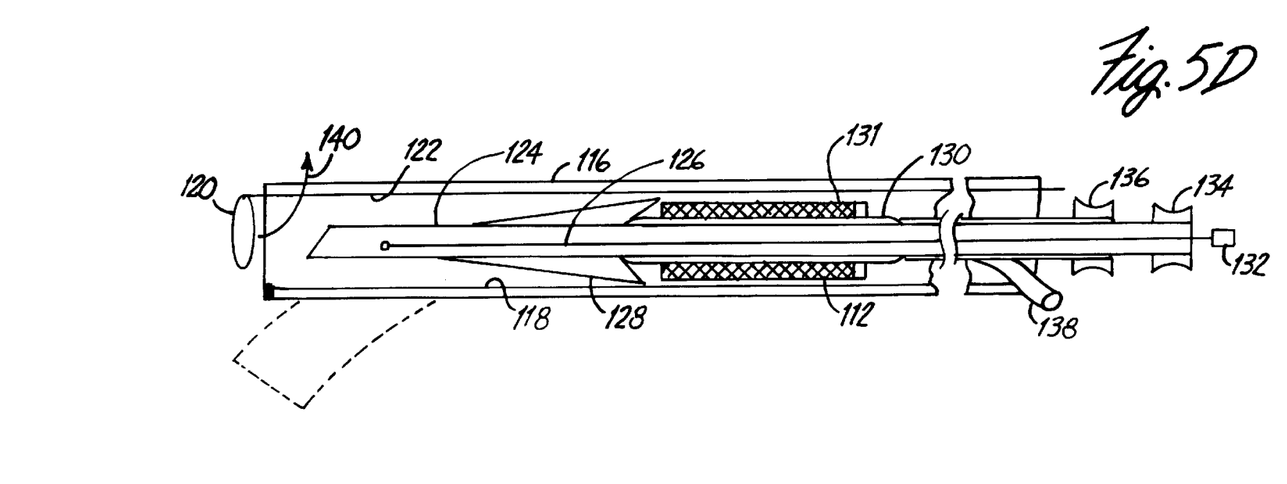
Figure 5E:
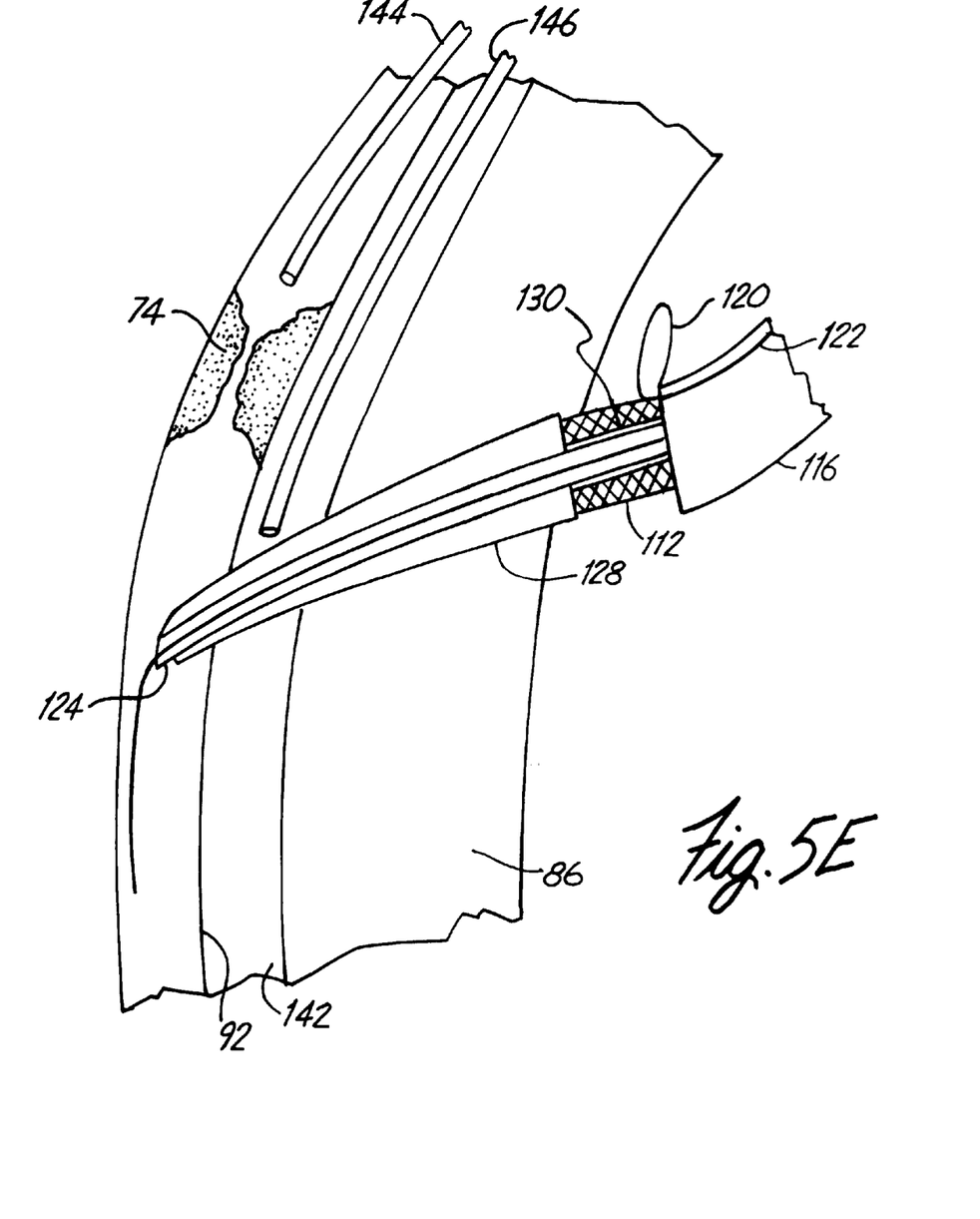
Figure 5F:
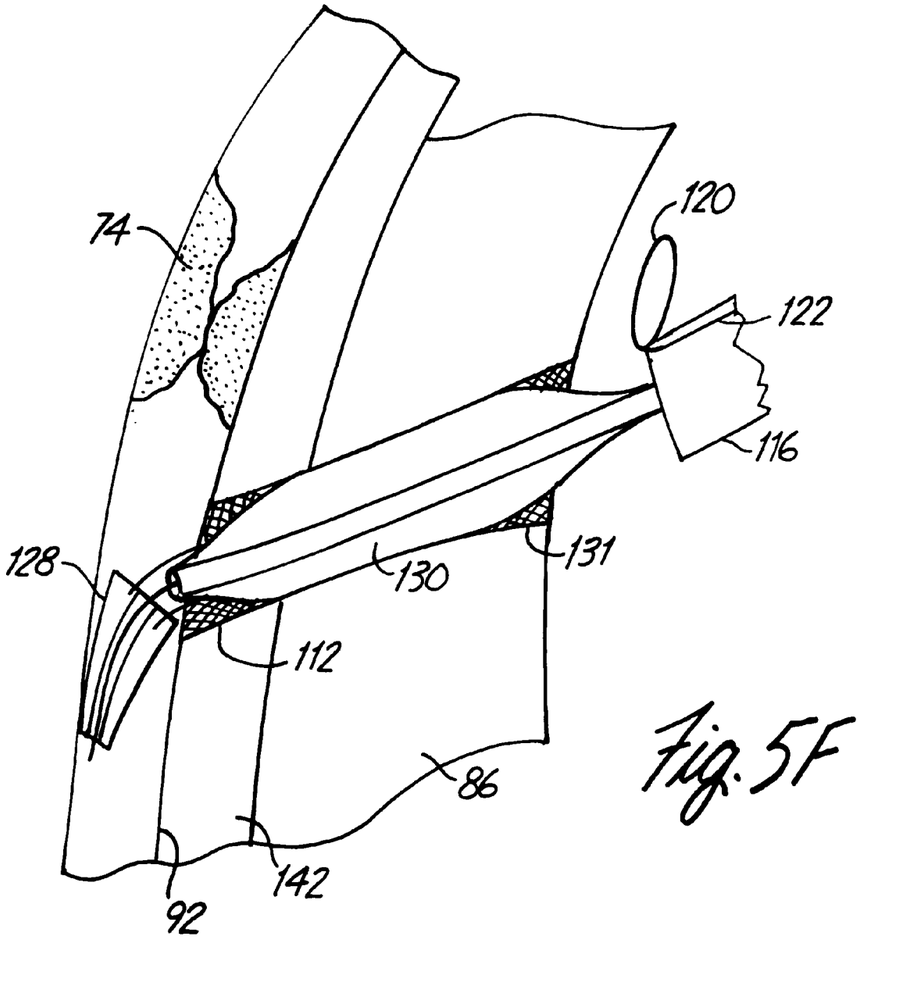

FIGS. 5D–5F illustrate such a system. FIG. 5D illustrates a deflectable guide catheter 116. Guide catheter 116 has, disposed therein and attached at a distal end thereof, pull wire 118. FIG. 5D also illustrates that guide catheter 116 has disposed at the distal end thereof light sensor (either a light emitter or a light detector) 120. Light sensor 120 is coupled to a torque wire 122 which also extends within catheter 116. A cutting catheter or needle 124 is also illustrated in FIG. 5D. Cutting catheter 124 has an inner lumen which is suitable for tracking over a guidewire 126. Dilator sheath 128 is disposed on the exterior of cutting catheter 124. Proximal of dilator sheath 128, stent 112 is disposed over inflatable balloon 130. Valve 131 is shown disposed on stent 112. The proximal end of the system shown in FIG. 5D includes a handle or actuator 132 coupled for manipulation of guidewire 126. Needle control manifold 134 is coupled to needle or cutting catheter 124, and dilator sheath control manifold 136 is coupled to dilator sheath 128. Also, the proximal end includes inflation coupling 138 which is coupled to an inflation lumen for inflating balloon 130.

Pull wire 118 is movable within guide catheter 116, except that it is coupled to the distal end of guide catheter 116. Therefore, by pulling on the proximal end of pull wire 118, guide catheter 116 can be deflected such that the distal end is disposed at an angle with respect to the remainder of guide catheter 116, as illustrated in phantom in FIG. 5D.

Light sensor 120 is pivotable relative to guide catheter 116 with torque wire 122. Therefore, torque wire 122 can be pivoted at its proximal end (or torqued) causing a force to be exerted on light sensor 120 which tends to cause light sensor 120 to pivot with torque wire 122 in the direction generally indicated by arrow 140. Thus, light sensor 120 can be maintained at the distal end of guide catheter 116 during sensing and positioning of guide catheter 116. It can then be pivoted out of the way to expose the inner lumen of guide catheter 116, and cutting catheter 124, after guide catheter 116 has been suitably positioned.

FIGS. 5E and 5F further illustrate the employment of the system shown in FIG. 5D. In FIG. 5E, the distal end of guide catheter 116 is shown positioned proximate heart tissue 86. FIG. 5E also shows the restricted lumen having restriction 74 therein, along with a coronary vein 142. In the preferred embodiment, a pair of light sources 144 and 146 are inserted in the restricted vessel proximal of restriction 74, and in the coronary vein 142 at an area just distal of restriction 74. Then, the distal end of guide catheter 116 is positioned using light sensor 120 adjacent heart tissue 86 at a position just proximal of restriction 74. Torque wire 122 is then rotated to pivot light sensor 120 out of adjacent location with the distal end of the lumen of guide catheter 116. Next, cutting catheter 124 is advanced out of the distal end of guide catheter 116 and is used to pierce through heart tissue 86, coronary vein 142 and vessel wall 92. Cutting catheter 124 can then be removed from the system, or it can be retained in place. In any case, dilator sheath 128 is passed over guidewire 126 and is advanced through the incision made by cutting catheter 124 to dilate the incision. Stent 112, along with inflatable balloon 130 is then advanced into the incision behind dilator sheath 128. Balloon 130 is then inflated to deploy stent 112.

Deployment of stent 112 is illustrated in FIG. 5F. Once stent 112 is deployed, both balloon 130 and dilator sheath 128, as well as the remainder of the assembly, can be removed leaving stent 112 and valve 131 in place.

FIGS. 5G–5J illustrate additional aspects of the present invention in accordance with other preferred embodiments.

Figure 5G:
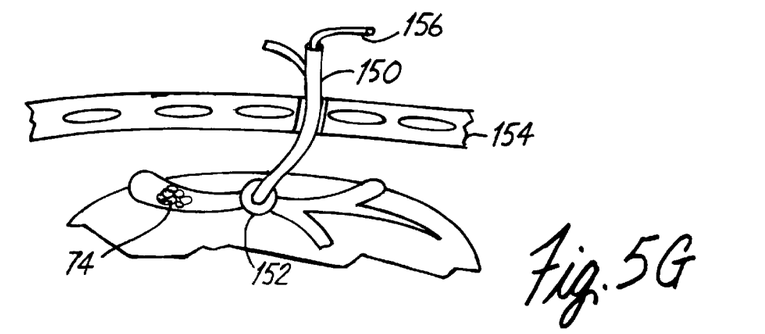

In FIG. 5G, steerable catheter 150 has a suction device or vacuum device 152 disposed at the distal end thereof. A small aperture is formed in the chest 154 of the patient, and steerable catheter 150 is inserted therein and used in conjunction with a fiber optic scope 156. Catheter 150 is moved under observation through scope 156 into a position just distal of stenosis 74. In another preferred embodiment, fluoroscopy may also be used for placement of suction device 152 with respect to stenosis or restriction 74. Once the distal end of catheter 150 is centered on the artery distal of restriction 74, a vacuum is exerted through suction device 152 to maintain the distal end of catheter 150 in place throughout the procedure. Scope 156 is then removed from catheter 150.

Figure 5H:
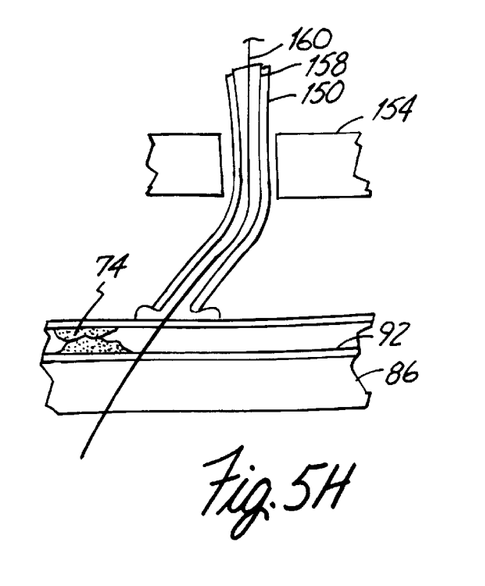

FIG. 5H illustrates that a small centering catheter 158 is then placed within catheter 150. Centering catheter 150 is used to center a wire 160 which is then placed therein. The thin wire 160 is then tracked through the center of catheter 150 and centering catheter 158 toward the artery. Wire 160 is then pushed through the exterior and interior walls of the artery, through the myocardium, and into either the ventricle or the atrium.

Figure 5I:
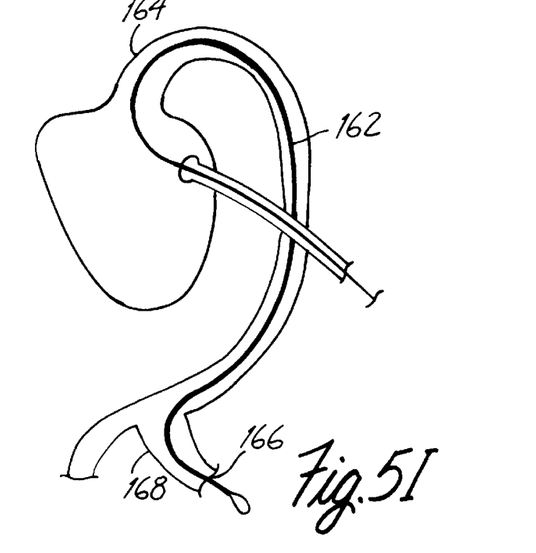

Wire 160 is then removed and replaced with a conventional spring tip guidewire, illustrated by the designation numeral 162 in FIG. 5I. Guidewire 162 is advanced through the myocardium and into the ventricle. Wire 162 is then tracked through the ascending aorta 164 to an exit point 166 in femoral artery 168. The lumen between the ventricle and the artery is then sized with, for example, an RF ablation wire. This is more specifically illustrated in FIG. 5J.

Figure 5J:
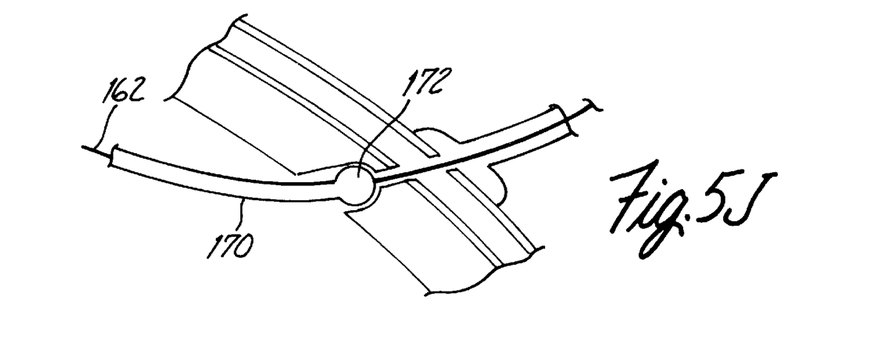

A catheter 170 is advanced over guidewire 162 from the femoral artery to the heart chamber. Catheter 170 preferably includes a burr 172 at its distal end which is appropriately sized to form the desired lumen. Burr 172 is placed against the wall of the vessel and the RF ablation portion of catheter 170 is energized such that muscle is ablated as burr 172 is advanced from the chamber to the artery creating a smooth lumen. Again, in the preferred embodiment, the lumen between the heart chamber and the restricted vessel is preferably disposed at an angle approximately 45° relative to the restricted vessel to accomplish a smooth flow transition between the chamber and the artery distal of the restriction.

Figure 6:
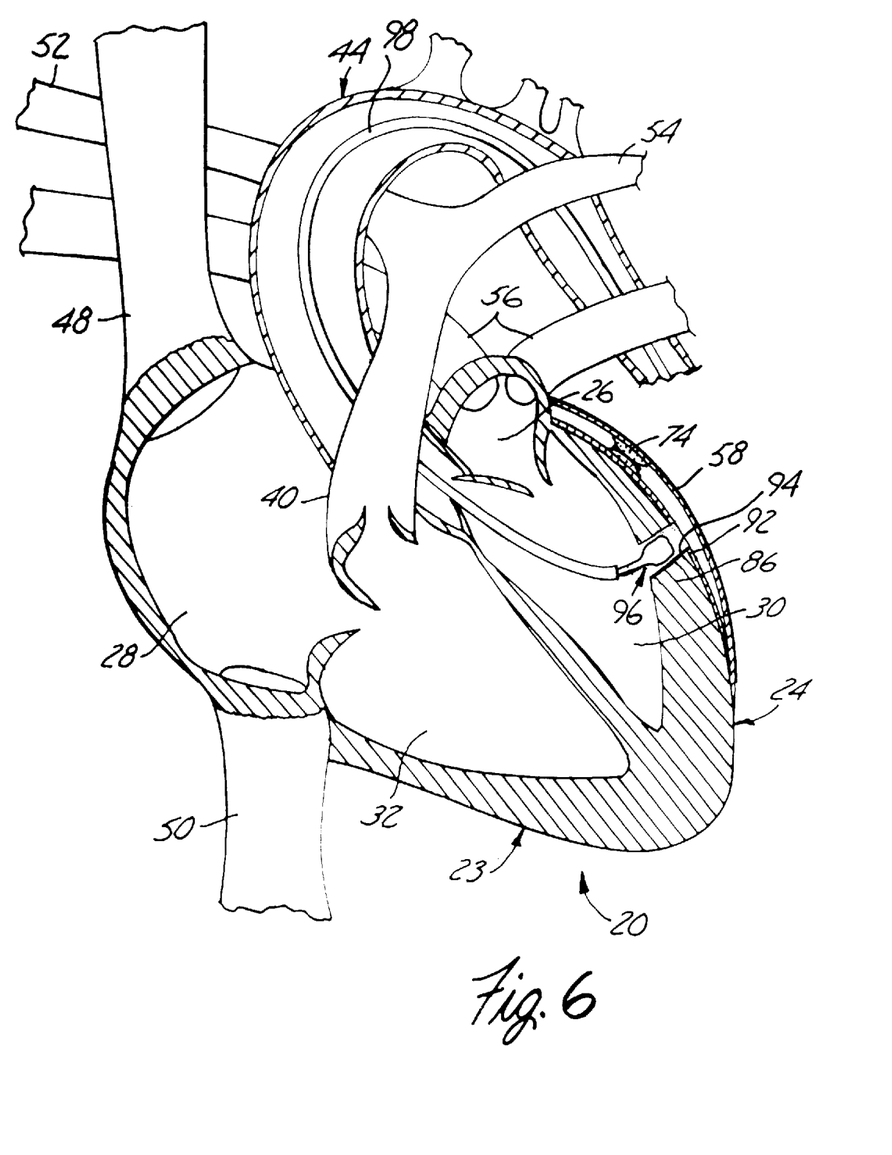
FIG. 6 illustrates a partially sectioned view of the heart of FIG. 1 and another step of an embodiment in accordance with the present invention.

FIG. 6 illustrates another step in accordance with one preferred embodiment of the present invention. In FIG. 5, the lumen between the heart chamber and the restricted vessel has been formed and the cutting device has been withdrawn from aorta 44 through guide catheter 80. FIG. 6 illustrates that drug delivery device 96 has been advanced through guide catheter 98, the aorta 44 and into the left ventricle 30 into the lumen 94. Drug delivery device 96 is preferably any suitable and known drug delivery device, such as a microcatheter, a perforated balloon delivery device, or any other suitable device. In the preferred embodiment, drug delivery device 96 is used to deliver a drug to lumen 94 to enhance endothelial development in lumen 94. In one preferred embodiment, the substance delivered to lumen 94 with delivery device 96 includes a growth factor which enhances the growth of endothelial cells on the wall of lumen 94. In another preferred embodiment, the substance delivered to lumen 94 with delivery device 96 includes endothelial cells which enhance endothelialization in lumen 94.

Further, in one embodiment, blood flow through coronary artery 58 is stopped during the procedure. One system for stopping blood flow includes occluding balloons. Occluding balloons have a fairly low instance of emboli formation, and therefore have a fairly low instance of neurological problems which result from the formation of emboli.

Thus, it can be seen that, by tunneling through the coronary artery vessel wall 92 and heart tissue 86 to form a lumen 94 that communicates with a chamber of the heart and distal arterial bed 78, restriction 24 is effectively bypassed.

Figure 7A:
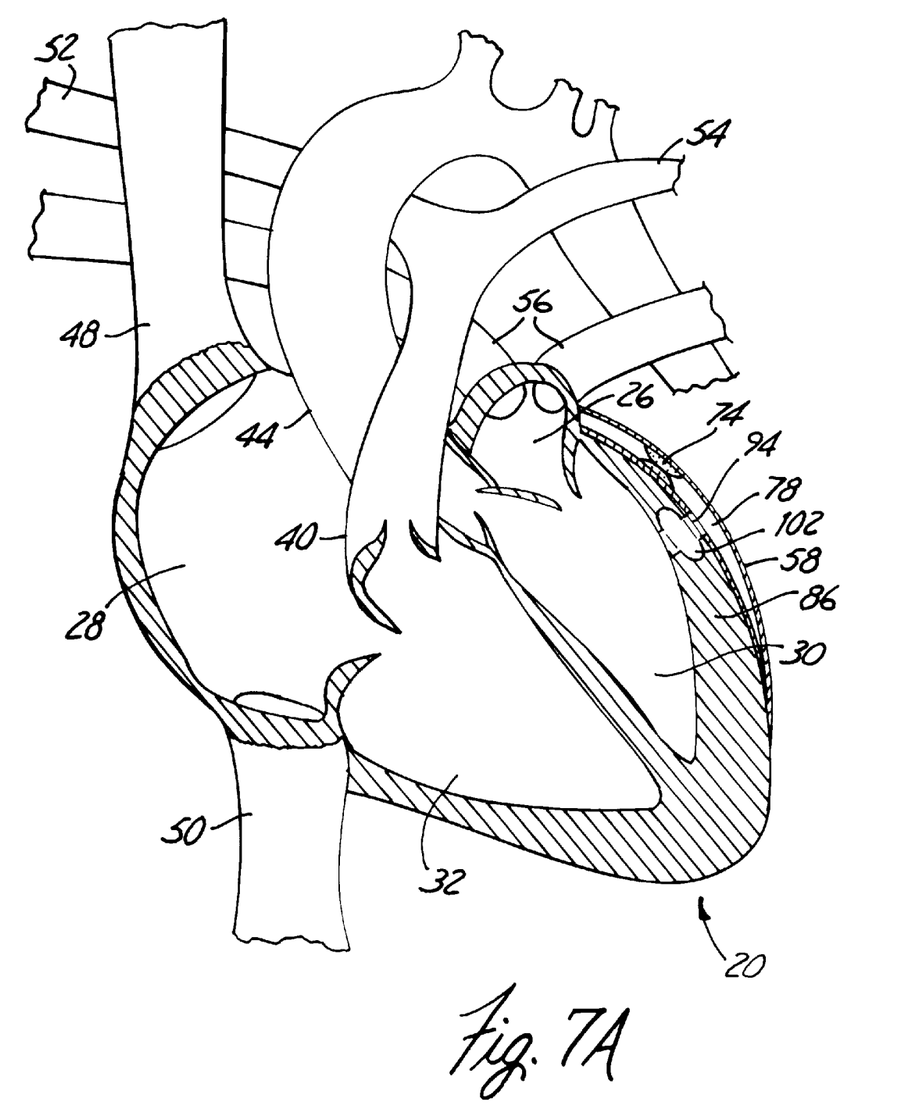
FIGS. 7A–7B illustrate a partially sectioned view of the heart of FIG. 1 and another step of an embodiment in accordance with the present invention.

FIG. 7A shows another embodiment of the present invention. Cutting device 84 has fashioned a reservoir 102 in the heart tissue 86 which communicates with lumen 94. As the chamber fills with blood, so does the reservoir 102. The contracting action of the heart 20 forces blood from the reservoir and into the distal arterial bed 78.

Figure 7B:
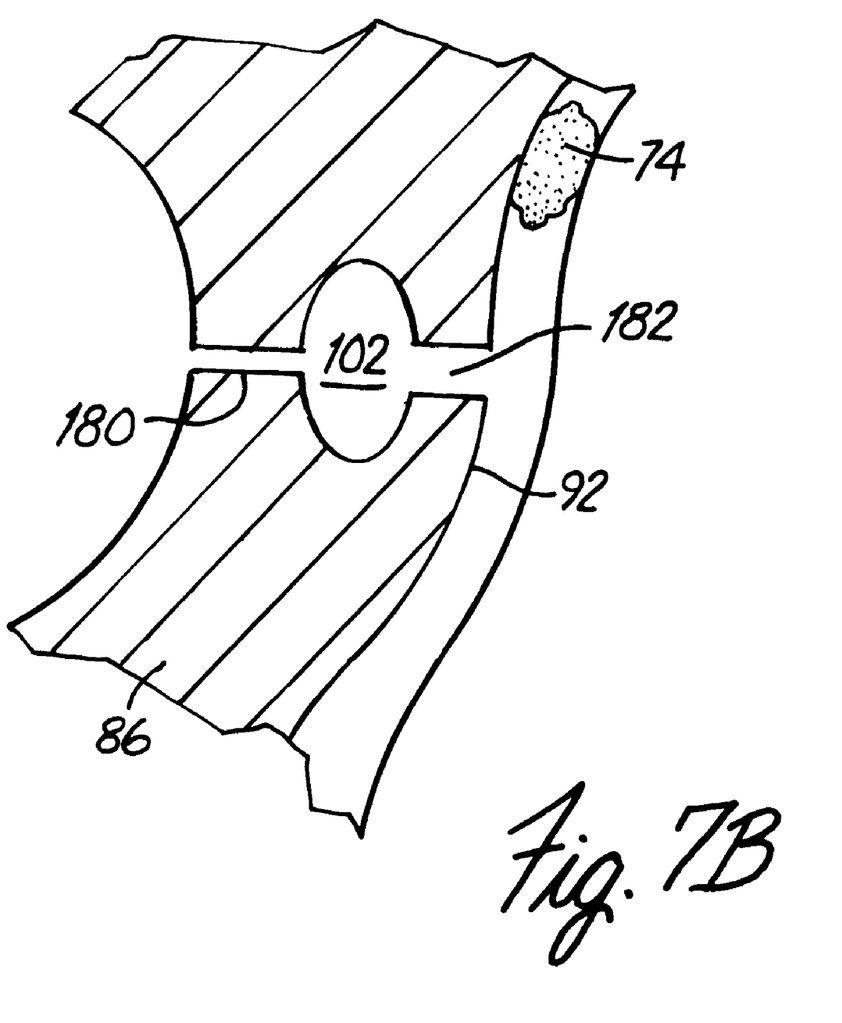

FIG. 7B is an enlarged view of reservoir 102. FIG. 7B illustrates that reservoir 102 has an inlet lumen 180 leading from the heart chamber to reservoir 102, and an outlet lumen 182 leading from reservoir 102 through vessel wall 92 into the restricted vessel. In the preferred embodiment, inlet vessel 180 has a smaller diameter than outlet lumen 182. Thus, during contraction of the heart, blood in the reservoir 102 is preferentially directed outward via the larger outlet lumen 182 into the restricted vessel. This reduces any back-flow which could occur from reservoir 102 back into the heart chamber via the inlet lumen 180, which has a smaller diameter.

Although the present invention has been described with reference to preferred embodiments, workers skilled in the art will recognize that changes may be made in form and detail without departing from the spirit and scope of the invention.

What is claimed is:

1. A method of bypassing a restriction in a coronary artery having an artery wall defining an artery lumen, the coronary artery lying adjacent heart tissue in a heart and proximate a heart chamber defining a heart chamber cavity, the method comprising:

accessing the heart chamber cavity;

forming a bypass lumen from the heart chamber cavity outward through the heart tissue and adjacent artery wall to the artery lumen distal of the restriction, wherein the heart chamber cavity communicates with the artery lumen distal of the restriction; and forming a reservoir in the heart tissue which communicates with the bypass lumen.

2. The method of claim 1 wherein forming a reservoir comprises:

forming an inlet lumen having a first diameter in the heart tissue, the inlet lumen being in fluid communication with the chamber cavity;

forming the reservoir; and forming an outlet lumen between the reservoir and the artery lumen, the outlet lumen having a second diameter, larger than the first diameter.

3. A method of bypassing a restriction in a coronary artery having an artery wall and a distal arterial bed distal of the restriction, wherein the coronary artery lies adjacent a heart on a heart wall, the heart having a plurality of chambers, each chamber defining a heart chamber cavity, the method comprising:

accessing with a guide catheter a heart chamber cavity;

advancing a cutting device through the guide catheter and to the heart wall proximate the distal arterial bed;

cutting from the heart chamber cavity outward through the heart wall and adjacent artery wall with the cutting device such that the heart chamber cavity communicates with the distal arterial bed through a bypass lumen; and forming a reservoir in the bypass lumen.

\* \* \* \* \*